(12) United States Patent
Metz

(10) Patent No.: US 8,485,197 B2
(45) Date of Patent: Jul. 16, 2013

(54) DENTAL ORTHOTIC

(76) Inventor: James Metz, Columbus, OH (US)

( * ) Notice: Subject to any disclaimer, the term of this patent is extended or adjusted under 35 U.S.C. 154(b) by 353 days.

(21) Appl. No.: 12/846,988

(22) Filed: Jul. 30, 2010

(65) Prior Publication Data

US 2012/0028205 A1  Feb. 2, 2012

(51) Int. Cl.
*A61F 5/56* (2006.01)
*A61C 5/14* (2006.01)

(52) U.S. Cl.
USPC .......................................... 128/848; 128/859

(58) Field of Classification Search
USPC ............................ 128/859–862, 848; 433/6–7
See application file for complete search history.

(56) References Cited

U.S. PATENT DOCUMENTS 5,562,106 A * 10/1996 Heeke et al. ................... 128/848

OTHER PUBLICATIONS

Kato, Thie, Huynh, Miyawaki, and Lavigne, "Topical Review: Sleep Bruxism and the Role of Peripheral Sensory Influences," Journal of Orofacial Pain 2003; 191-213.
Van Lunteren and Dick, "Motor Unit Regulation of Mammalian Pharyngeal Dilator Muscle Activity," Journal of Clinical Investigation vol. 84, Aug. 1989, 577-585.
Tsuiki, Ryan, Lowe, Inoue, "Functional contribution of mandibular advancement to awake upper airway patency in obstructive sleep apnea," Sleep Breath 2007; 11: 245-251.
Rossetti, Araujo, Rossetti and Conti, "Association Between Rhythmic Masticatory Muscle Activity During Sleep and Masticatory Myofascial Pain: A Polysomnographic Study," Journal of Orofacial Pain vol. 22, No. 3, 2008, 190-200.
Huynh, Rompre, Montplaisir, Manzini, Okura and Lavigne, "Comparison of Various Treatments for Sleep Bruxism Using Determinants of Number Needed to Treat and Effect Size," The International Journal of Prosthodontics vol. 19, No. 5, 2006, 435-441.
Johal, Gill, Ferman and McLaughlin, "The effect of mandibular advancement appliances on awake upper airway and masticatory muscle activity in patients with obstructive sleep apnoea," Clinical Physiology and Functional Imaging (2007) 27, pp. 47-53.

* cited by examiner

*Primary Examiner* — Patricia Bianco
*Assistant Examiner* — Ophelia A Hawthorne
(74) *Attorney, Agent, or Firm* — Michael J. Gallagher; David J. Dawsey; Gallagher & Dawsey Co., LPA

(57) ABSTRACT

A dental orthotic covering a plurality of teeth is provided for improving various obstructive syndromes of the human upper airway. The orthotic may be relatively thickened on the lingual side of the orthotic, compared to the facial or occlusal side; and in particular may relatively thickened in the more posterior aspects of the lingual side of the orthotic as compared to the more anterior aspects of the lingual side of the orthotic. The orthotic may be formed of one piece or two, and may be purely mandibular, or may be coupled to a maxillary orthotic. A method of progressive fitting of the orthotic for optimization of a patient's blood oxygen level is described.

31 Claims, 11 Drawing Sheets

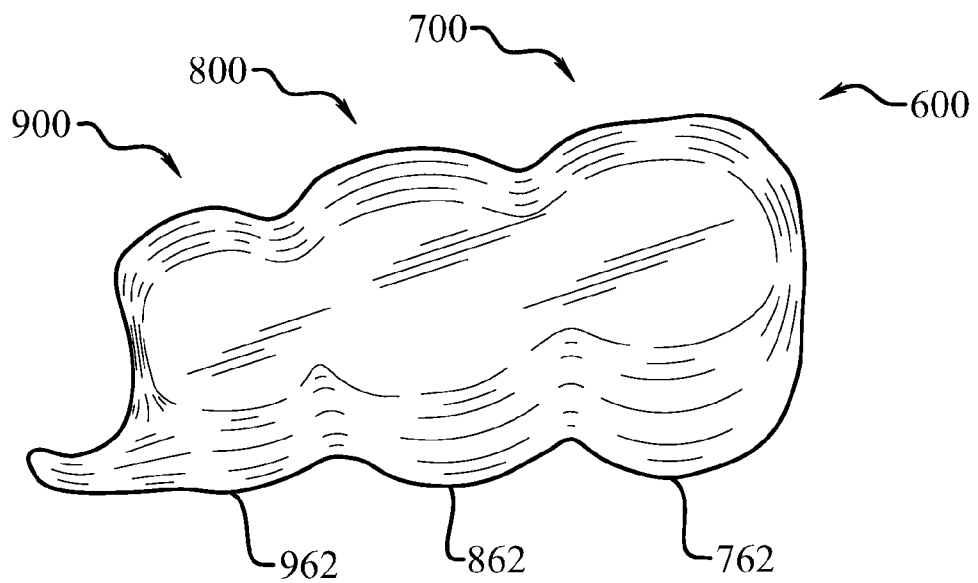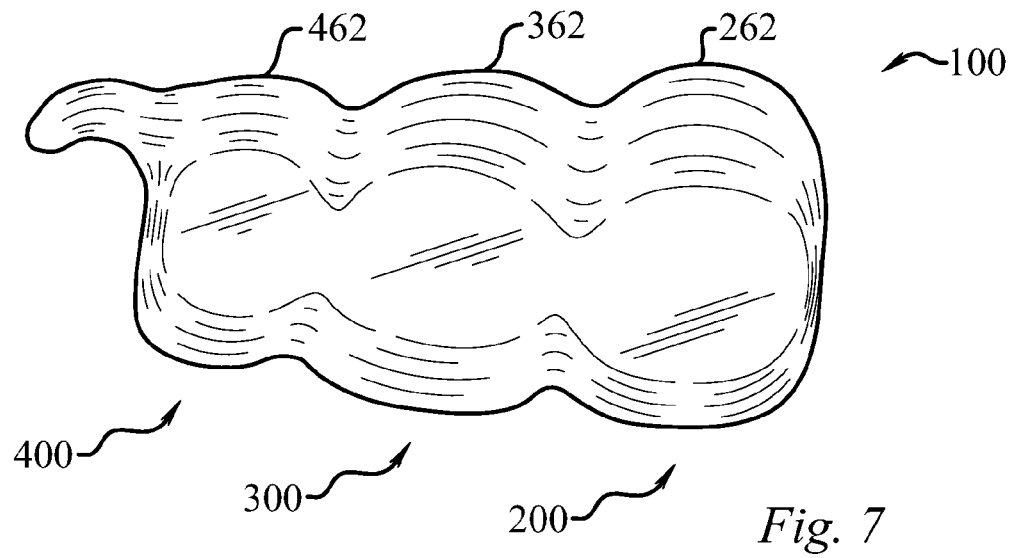
Fig. 7

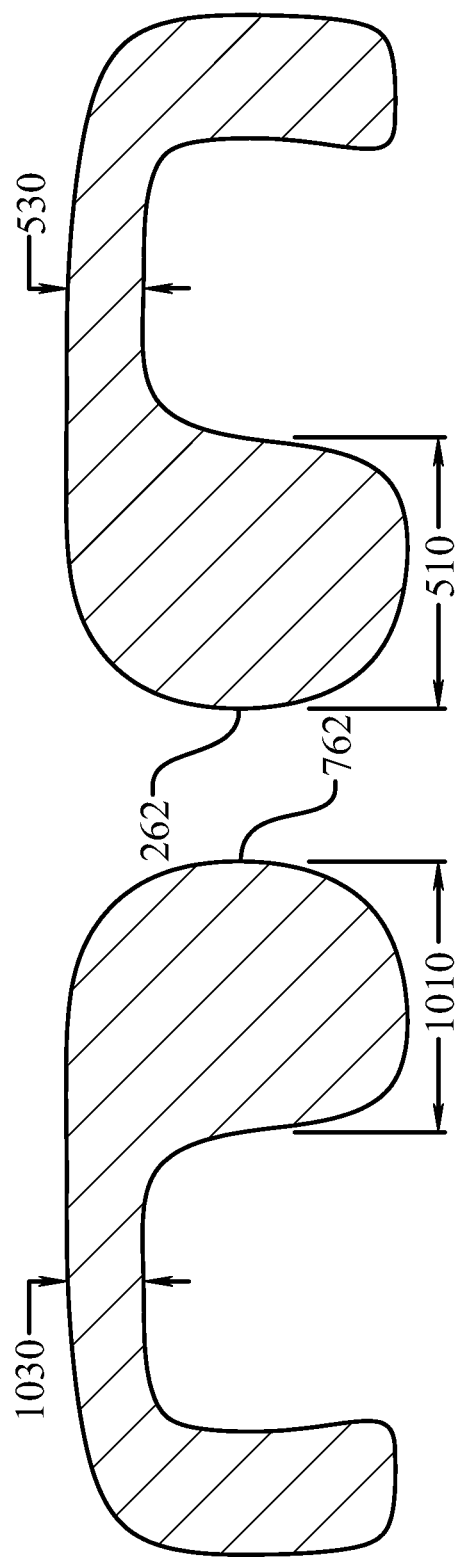

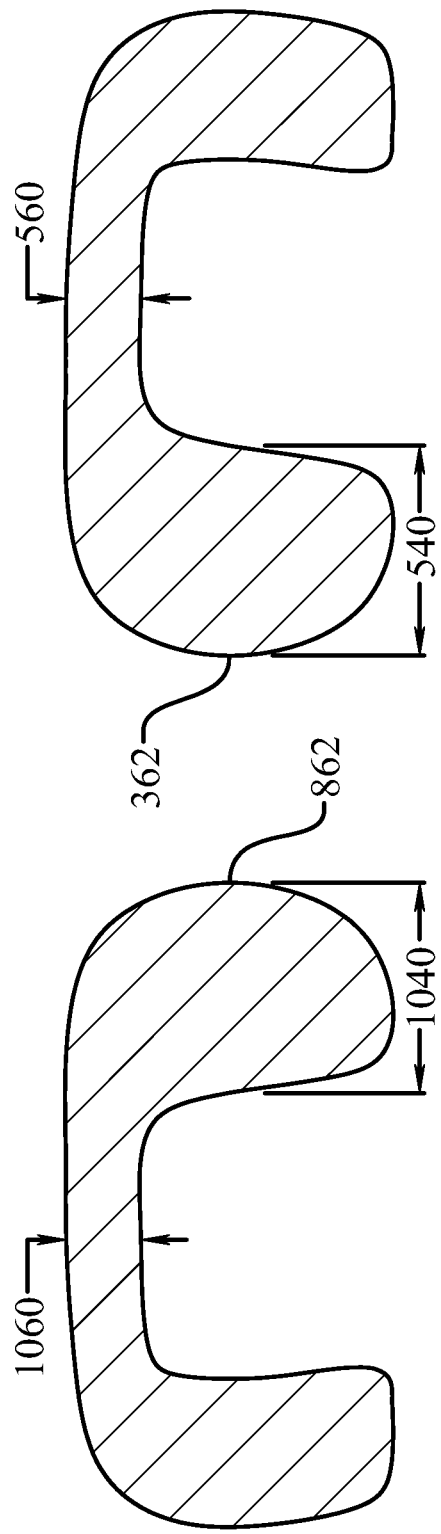

DENTAL ORTHOTIC

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD

The present disclosure relates generally to the field of dental orthotics, in particular, orthotics which affect the physiologic function of the upper airway.

BACKGROUND OF THE INVENTION

A large number of persons have varying degrees of upper airway obstruction presenting with varied degrees of symptoms. As the upper airway begins with the nose and mouth, it is not surprising that the nose, tongue, and jaw all make contributions to such obstructive syndromes.

Various treatment modalities have been suggested. Various airway pressure devices, such as continuous positive airway pressure devices (CPAP) have been successfully used, although these tend to be both cumbersome and uncomfortable. More recently, dental orthotics have been employed. One general class of orthotic relies upon shifting the position of the lower jaw, generally moving the jaw forward, to displace the tongue anteriorly and thereby help clear the upper airway. Obviously, it is difficult to shift the jaw anteriorly without an external anchor point, so these orthotic have also presented problems of utility and comfort.

Another class of orthotic, and in particular that described by Robson (U.S. Pat. No. 5,752,822) relies on positioning the tongue on an extension that elevates the tongue and causes the tongue to move forward to an upward position resting on the extension.

SUMMARY OF THE INVENTION

In its most general configuration, the presently disclosed dental orthotic advances the state of the art with a variety of new capabilities and overcomes many of the shortcomings of prior methods in new and novel ways. In its most general sense, the presently disclosed dental orthotic overcomes the shortcomings and limitations of the prior art in any of a number of generally effective configurations.

The dental orthotics described herein have at least a sinistral segment and a dextral segment. The orthotic fits over a plurality of teeth, and therefore has a number of segments and surfaces. Since the orthotic must generally conform to the anatomy of the plurality of teeth, these segments and surfaces are somewhat irregular shaped and bounded, in conformance with the natural anatomical surfaces of the teeth.

The sinistral segment further comprises a first sinistral cap segment having among its many surfaces, at least a sinistral external cap segment lingual surface and at least a first sinistral external cap segment facial surface. As is discussed in detail below, the sinistral external cap segment lingual surface is made, in one embodiment, thicker than the first sinistral external cap segment facial surface. A similar construction may be made in the dextral segment. In other embodiments, multiple segments having multiple sub-segments of both the sinistral segment and the dextral segment are provided, such that segments more posterior in the mouth may have external cap lingual surfaces that are relatively thicker than those more anterior in the mouth.

In a preferred embodiment, the orthotic is a mandibular orthotic and may have the sinistral and dextral segments coupled to one another. Additionally, in some embodiments, the mandibular orthotic may be coupled in part to a maxillary orthotic.

A method for making a dental orthotic is described, including the steps of molding the orthotic to the teeth, usually a plurality of molars. A patient with upper airway obstructive symptoms is then monitored for blood oxygen saturation while in a succession of steps, the orthotic is removed and additional material added to one of more of the external cap segment lingual surfaces and then replaced on the patient's teeth. Between each addition of material, the patient is observed for improvement in his or her blood oxygen concentration, and the addition of material is stopped when successive additions fail to produce an improvement in the blood oxygen concentration.

Numerous variations, modifications, alternatives, and alterations of the various preferred embodiments, processes, and methods may be used alone or in combination with one another as will become more readily apparent to those with skill in the art with reference to the following detailed description of the preferred embodiments and the accompanying figures and drawings.

BRIEF DESCRIPTION OF THE DRAWINGS

Without limiting the scope of the dental orthotic as disclosed herein and referring now to the drawings and figures:

FIG. 7 is a top view of another embodiment of a dental orthotic;

FIG. 9 is a section view of a dental orthotic taken through section line 9-9 of FIG. 8;

FIG. 10 is a section view of a dental orthotic taken through section line 10-10 of FIG. 8;

FIG. 11 is a section view of a dental orthotic taken through section line 11-11 of FIG. 8;

FIG. 12 is a section view of a dental orthotic taken through section line 12-12 of FIG. 8;

Figure 1:
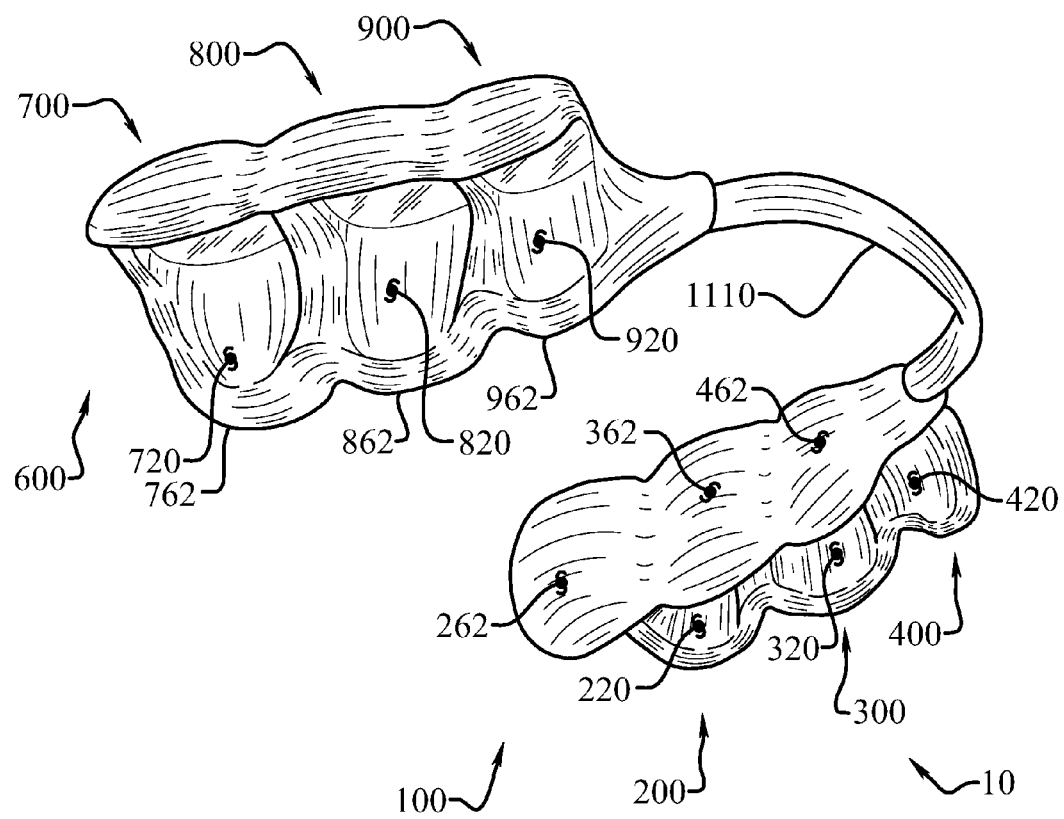
FIG. 1 is an inferior perspective view of a dental orthotic.

These drawings are provided to assist in the understanding of the exemplary embodiments of the invention as described in more detail below and should not be construed as unduly limiting the dental orthotic. In particular, the relative spacing, positioning, sizing and dimensions of the various elements illustrated in the drawings are not drawn to scale and may have been exaggerated, reduced or otherwise modified for the purpose of improved clarity. Those of ordinary skill in the art will also appreciate that a range of alternative configurations have been omitted simply to improve the clarity and reduce the number of drawings.

DETAILED DESCRIPTION OF THE INVENTION

The presently disclosed dental orthotic (10) enables a significant advance in the state of the art. The preferred embodiments of the dental orthotic (10) accomplish this by new and novel arrangements of elements and methods that are configured in unique and novel ways and which demonstrate previously unavailable but preferred and desirable capabilities. The description set forth below in connection with the drawings is intended merely as a description of the presently preferred embodiments of the dental orthotic (10), and is not intended to represent the only form in which the dental orthotic (10) may be constructed or utilized. The description sets forth the designs, functions, means, and methods of implementing the dental orthotic (10) in connection with the illustrated embodiments. It is to be understood, however, that the same or equivalent functions and features may be accomplished by different embodiments that are also intended to be encompassed within the spirit and scope of the claimed dental orthotic (10).

With reference generally to FIGS. 1-14, a dental orthotic (10) includes at least a sinistral segment (100) and a dextral segment (600). The orthotic (10) fits over a plurality of teeth, and therefore has a number of segments and surfaces, seen well in FIG. 1. Since the orthotic (10) must generally conform to the anatomy of the plurality of teeth, these segments and surfaces are somewhat irregular shaped and bounded, in conformance with the natural anatomical surfaces of the teeth.

Figure 2:
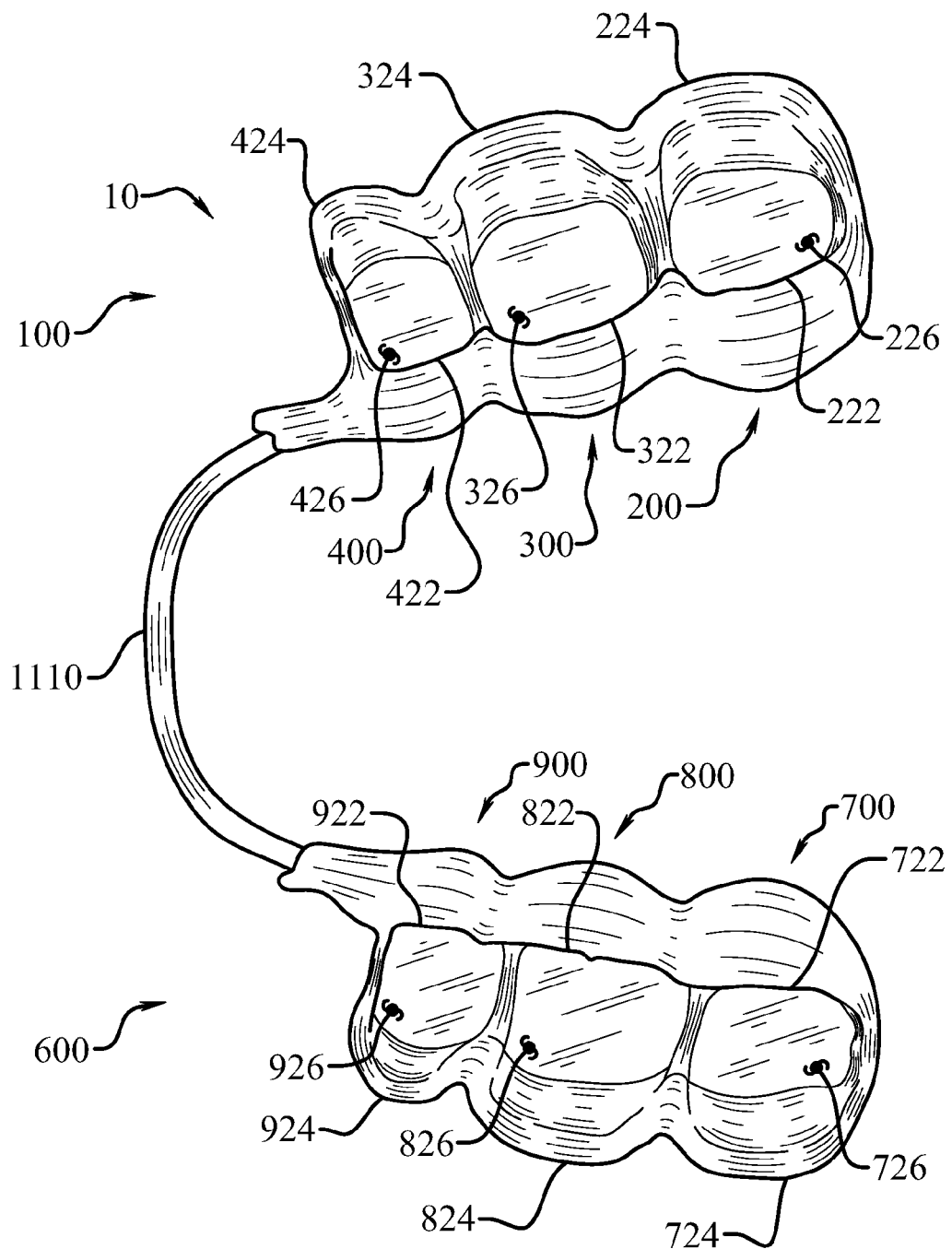
FIG. 2 is a bottom view of the orthotic of FIG. 1.
Figure 3:
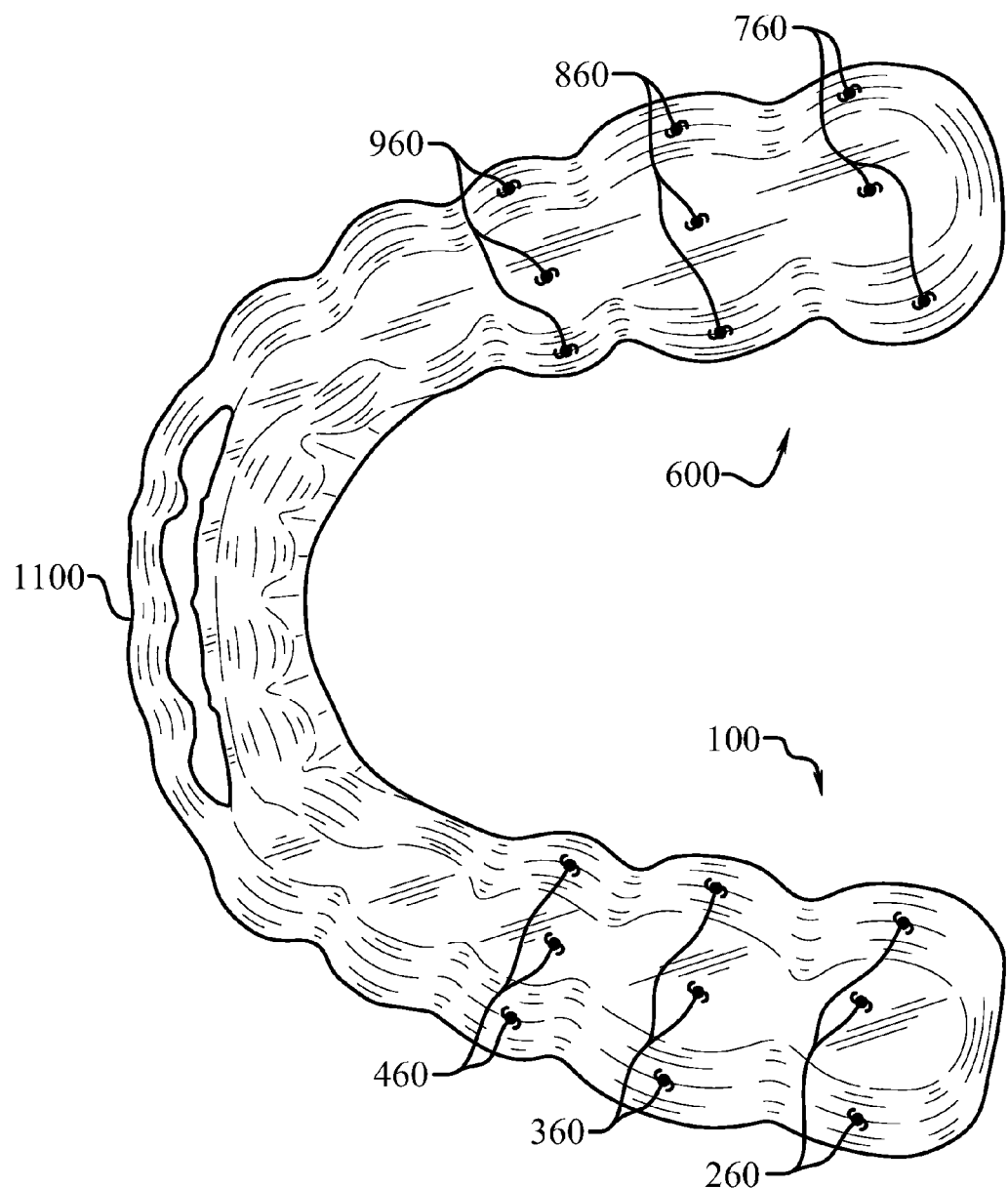
FIG. 3 is another top view of a dental orthotic.

The sinistral segment (100), as seen well in FIGS. 1, 2, and 3, may further include a first sinistral cap segment (200) having a first sinistral internal cap segment surface (220) which is in contact with a tooth, a first sinistral external cap segment surface (260). There may be at least one sinistral cap segment thickness (500), formed collectively by elements (510, 520), seen in FIG. 6, and (530), seen in FIG. 10; defined as the thickness of the orthotic (10) material occupying the distance between the first sinistral internal cap segment surface (220) and the first sinistral external cap segment surface (260), seen in FIGS. 1 and 3.

The internal surface, that is, the first sinistral internal cap segment surface (220), seen well in FIG. 1, further may have various subdivisions, seen in FIG. 2, including a first sinistral internal cap segment lingual surface (222), a first sinistral internal cap segment facial surface (224), and a first sinistral internal cap segment occlusal surface (226), named in accordance with the standard dental charting nomenclature for the corresponding tooth surface with which these surfaces (222, 224, 226) are in contact. The close fit between these surfaces (222, 224, 226), seen in FIG. 2, and the corresponding tooth surfaces at least in part, assists with keeping the orthotic (10) in its proper operative position.

Figure 5:
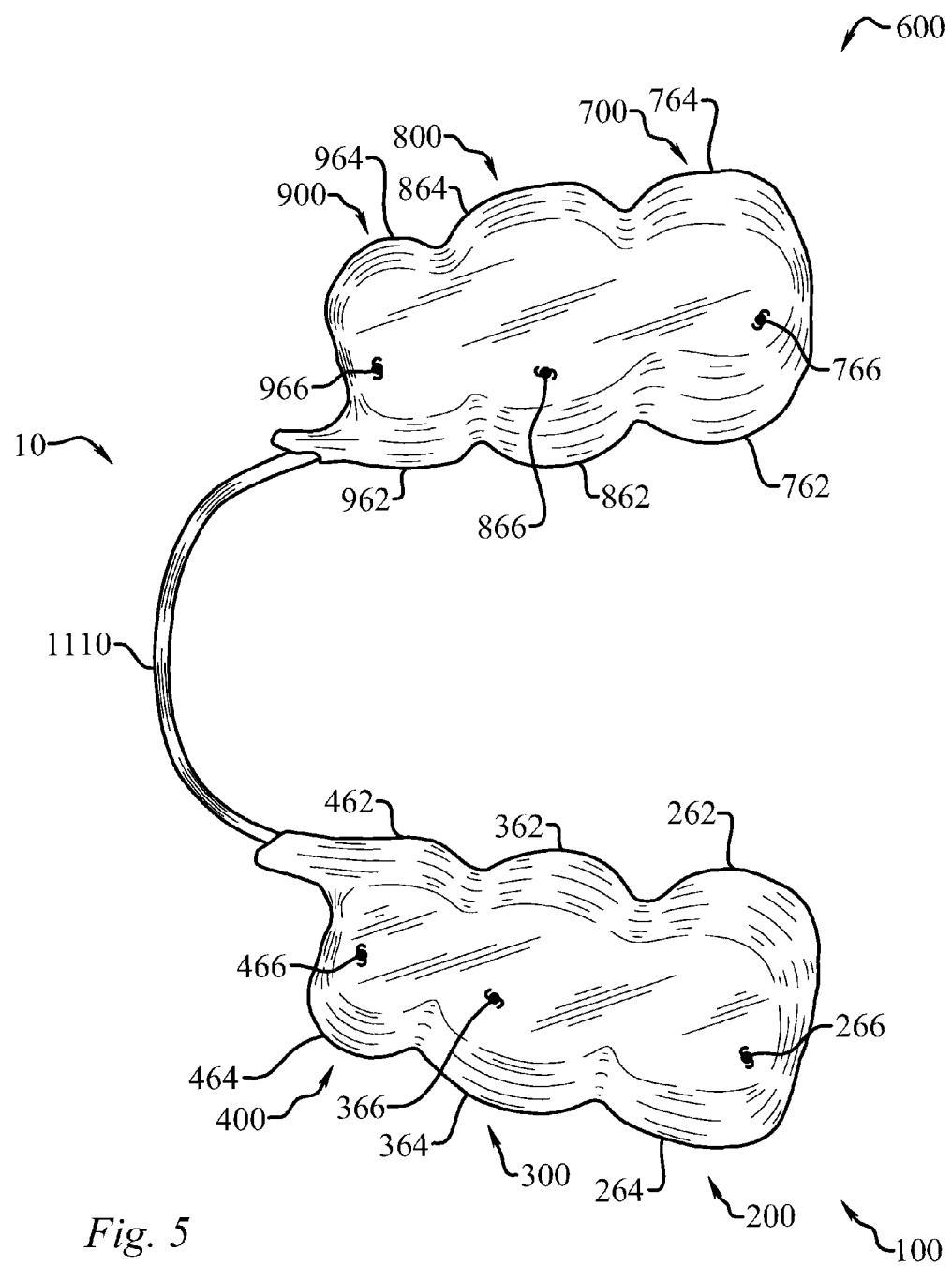
FIG. 5 is a top view of the dental orthotic of FIG. 1.

The first sinistral external cap segment surface (260), seen well in FIG. 3, likewise may have various surfaces, seen in FIG. 5, and includes a first sinistral external cap segment lingual surface (262), first sinistral external cap segment facial surface (264), and a first sinistral external cap segment occlusal surface (266).

Figure 6:
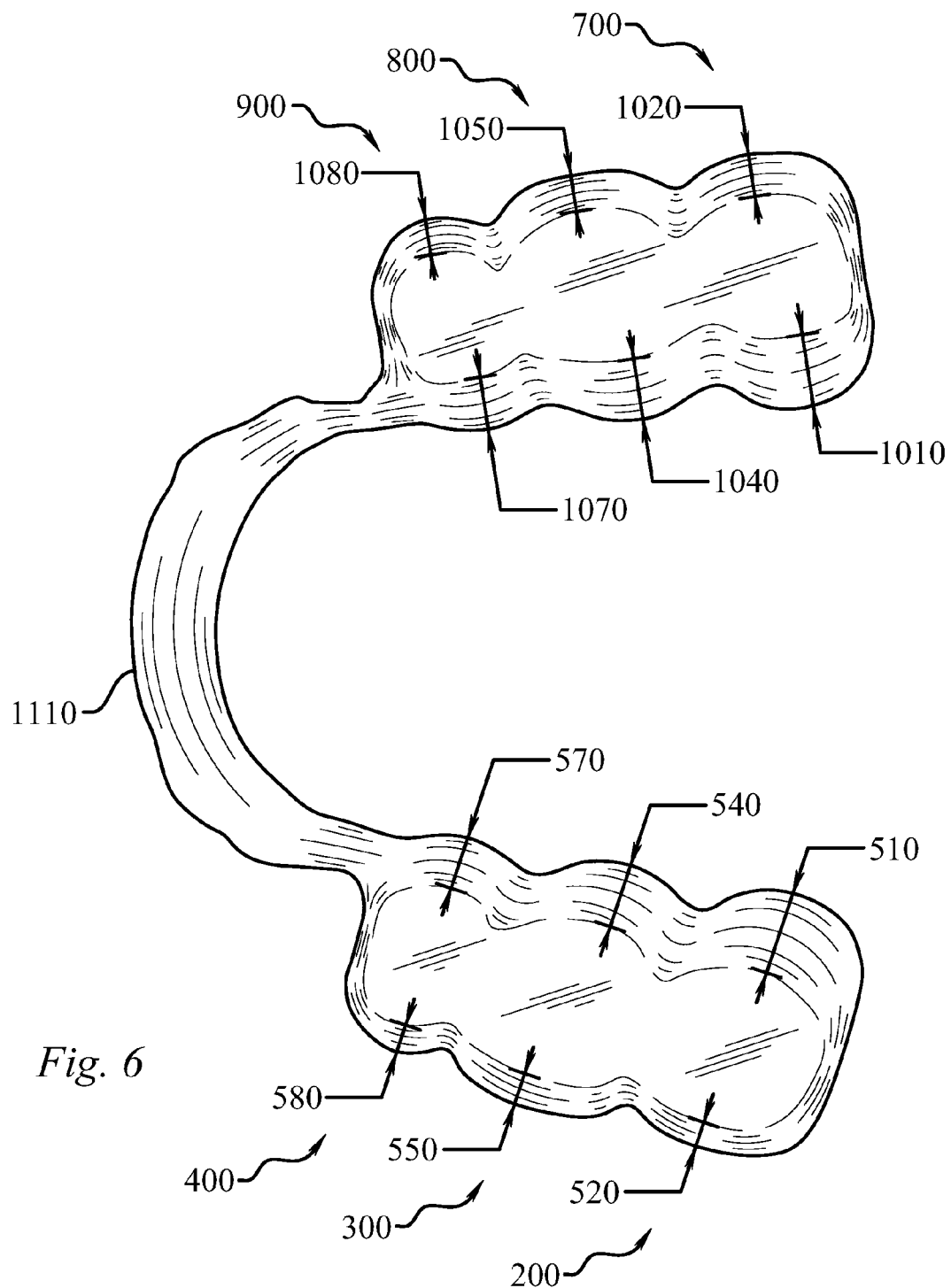
FIG. 6 is a top view of another embodiment of a dental orthotic.
Figure 8:
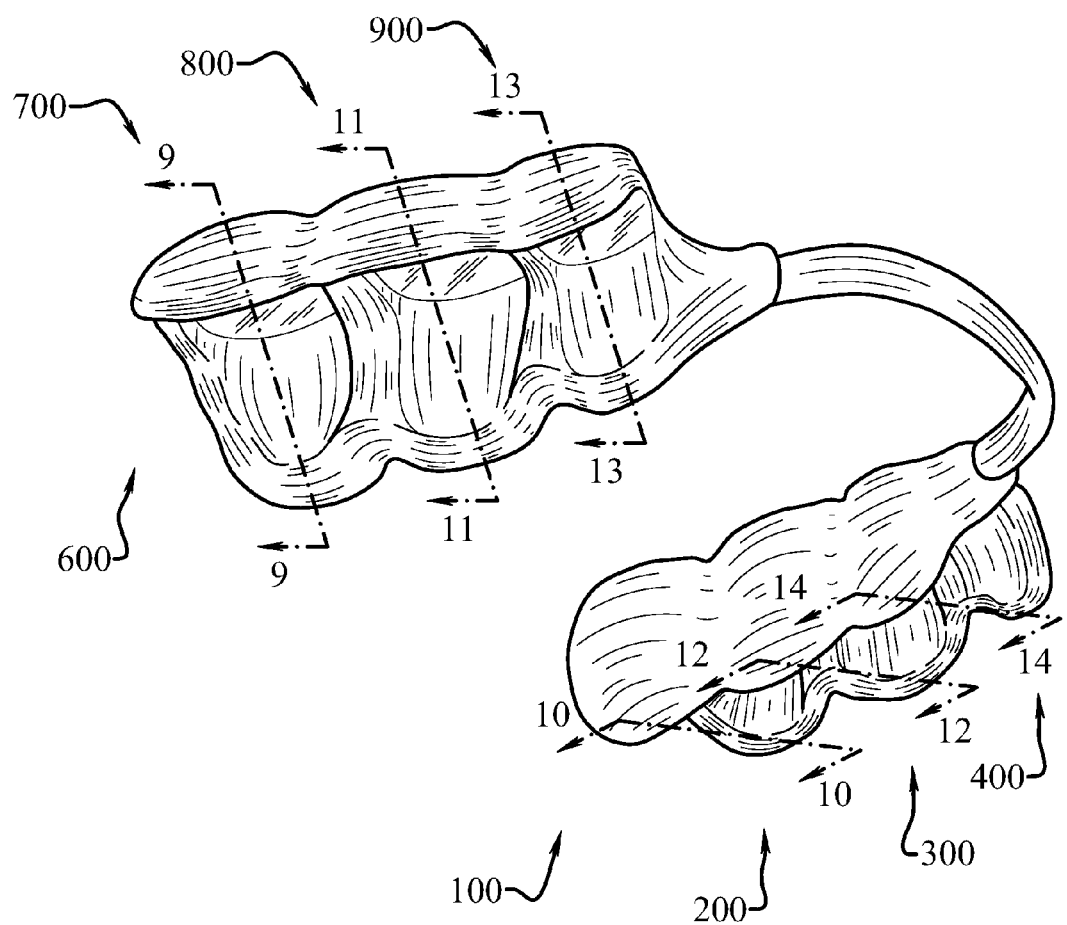
FIG. 8 is an another inferior perspective view of the dental orthotic of FIG. 1.

Various thicknesses, seen well in FIGS. 4, 6, and 8-14, are associated with the various surfaces, such that the sinistral cap segment thickness (500) is formed collectively by elements (510, 520), seen in FIG. 6, and (530), seen in FIG. 10, defined as the thickness of the orthotic (10) material occupying the distance between the first sinistral internal cap segment surface (220) and the first sinistral external cap segment surface (260), seen in FIGS. 1 and 3.

The sinistral cap segment thickness (500), may further include a first sinistral cap segment lingual thickness (510) and a first sinistral cap segment facial thickness (520), seen well in FIG. 6, and a first sinistral cap segment occlusal thickness (530), seen well in FIG. 10, again named in accordance with the standard dental charting nomenclature for corresponding tooth surfaces.

Various structures on the dextral segment (600), also seen well in FIGS. 1, 2, and 3, further correspond to those already discussed on the sinistral segment (100). The dextral segment (600) may include a first dextral cap segment (700) having a first dextral internal cap segment surface (720), seen in FIG. 1, and a first dextral external cap segment surface (760), seen in FIG. 3. There may be at least one dextral cap thickness (1000), formed collectively by elements (1010, 1020), seen in FIG. 6, and (1030) seen in FIG. 9; defined as the thickness, or distance, between the first dextral internal cap segment surface (720) and the first dextral external cap segment surface (760), as seen in FIGS. 1 and 3.

As seen in FIGS. 1 and 2, the first dextral internal cap segment surface (720) may further include a first dextral internal cap segment lingual surface (722), a first dextral internal cap segment facial surface (724), and a first dextral internal cap segment occlusal surface (726). Correspondingly, the first dextral external cap segment surface (760), seen in FIGS. 3 and 5, further comprises a first dextral external cap segment lingual surface (762), first dextral external cap segment facial surface (764), and a first dextral external cap segment occlusal surface (766). Various thicknesses are determined by relationships among these surfaces. For example, the dextral cap segment thickness (1000) further comprises a first dextral cap segment lingual thickness (1010) and a first dextral cap segment facial thickness (1020), seen in FIG. 6 and a first dextral cap segment occlusal thickness (1030), as seen in FIG. 9.

Typically, the first sinistral cap segment facial thickness (520), seen in FIG. 6, the first sinistral cap segment occlusal thickness (530), seen in FIG. 10, the first dextral cap segment facial thickness (1020), seen in FIG. 6, and the first dextral cap segment occlusal thickness (1030), seen in FIG. 9, are similar in thickness, with the thickness being primarily dictated by the need to provide strength to the orthotic. However, in a preferred embodiment, seen in FIG. 6, the first sinistral cap segment lingual thickness (510) may be greater than the first sinistral cap segment facial thickness (520), and the first dextral cap segment lingual thickness (1010) may be greater than the first dextral cap segment facial thickness (1020).

In various embodiments, seen well in FIGS. 1-3, the orthotic (10) may comprise more than one sub-segment within the sinistral segment (100). By way of example only, the sinistral segment (100) may include a second sinistral cap segment (300) having a second sinistral internal cap segment surface (320), a second sinistral external cap segment surface (360). There may be at least one sinistral cap segment thickness (500), formed collectively by elements (540, 550), as seen in FIG. 6, and (560), seen in FIG. 12; defined as the thickness of the orthotic (10) material, that is the distance between the second sinistral internal cap segment surface (320) and the second sinistral external cap segment surface (360), as seen in FIGS. 1 and 3.

In such embodiments, such as is seen in FIGS. 1 and 2, the second sinistral internal cap segment surface (320) may have a second sinistral internal cap segment lingual surface (322), a second sinistral internal cap segment facial surface (324), and a second sinistral internal cap segment occlusal surface (326). The second sinistral external cap segment surface (360), seen in FIG. 3, may include a second sinistral external cap segment lingual surface (362), second sinistral external cap segment facial surface (364), and a second sinistral external cap segment occlusal surface (366), as seen in FIG. 5.

The sinistral cap segment thickness (500), formed collectively by elements (540, 550), seen in FIG. 6, and (560) seen in FIG. 12, may further include a second sinistral cap segment lingual thickness (540), a second sinistral cap segment facial thickness (550), and a second sinistral cap segment occlusal thickness (560). The second sinistral cap segment lingual thickness (540) may be greater than the second sinistral cap segment facial thickness (550), as seen in FIG. 6.

Figures 13, 14:
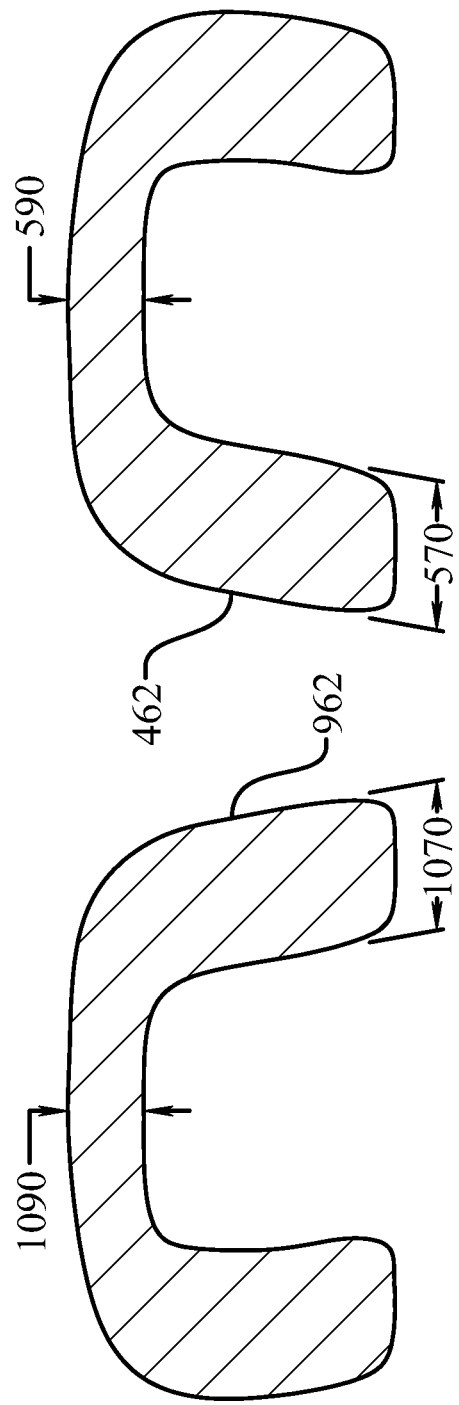
FIG. 13 is a section view of a dental orthotic taken through section line 13-13 of FIG. 8.
FIG. 14 is a section view of a dental orthotic taken through section line 14-14 of FIG. 8.

In yet other embodiments, again seen well in FIGS. 1-3, the sinistral segment (100) may also include a third sinistral cap segment (400) having a third sinistral internal cap segment surface (420), a third sinistral external cap segment surface (460) and at least one sinistral cap segment thickness (500), formed collectively by elements (570, 580), seen in FIG. 6, and (590), seen in FIG. 14; defined as the thickness of the orthotic (10) material, that is the distance between the third sinistral internal cap segment surface (420) and the third sinistral external cap segment surface (460), as seen in FIGS. 1 and 3.

In such embodiments, the third sinistral internal cap segment surface (420), seen in FIG. 1, can further include a third sinistral internal cap segment lingual surface (422), a third sinistral internal cap segment facial surface (424), and a third sinistral internal cap segment occlusal surface (426), as seen in FIG. 2. In such embodiments, the third sinistral external cap segment surface (460), seen in FIG. 3, can further include a third sinistral external cap segment lingual surface (462), third sinistral external cap segment facial surface (464), and a third sinistral external cap segment occlusal surface (466), seen in FIG. 5.

The sinistral cap segment thickness (500), formed collectively by elements (570, 580), seen in FIG. 6, and (590), seen in FIG. 14, can further include a third sinistral cap segment lingual thickness (570) and a third sinistral external cap segment facial thickness (580), seen in FIG. 6, and a third sinistral cap segment occlusal thickness (590), seen in FIG. 14. The third sinistral cap segment lingual thickness (570) may be greater than the third sinistral external cap segment facial thickness (580), again as seen in FIG. 6.

In yet additional embodiments, the dextral segment (600), seen in FIGS. 1 through 3, may further include a second dextral cap segment (800) having a second dextral internal cap segment surface (820) and a second dextral external cap segment surface (860). There may be at least one dextral cap segment thickness (1000), formed collectively by elements (1040, 1050), seen in FIG. 6, and (1060), seen in FIG. 11; defined as the thickness of the orthotic (10) material, as seen in FIGS. 1 and 3, that is the distance between the second dextral internal cap segment surface (820) and the second dextral external cap segment surface (860).

In such embodiments, the second dextral internal cap segment surface (820), seen in FIG. 1, can further include a second dextral internal cap segment lingual surface (822), a second dextral internal cap segment facial surface (824), and a second dextral internal cap segment occlusal surface (826), all as seen in FIG. 3. The second dextral external cap segment surface (860), seen in FIG. 3, may further have, as seen in FIG. 5, a second dextral external cap segment lingual surface (862), second dextral external cap segment facial surface (864), and a second dextral external cap segment occlusal surface (866).

The dextral cap segment thickness (1000) can further include a second dextral cap segment lingual thickness (1040), a second dextral cap segment facial thickness (1050), both as seen in FIG. 6, and a second dextral cap segment occlusal thickness (1060), as seen in FIG. 11; and the second dextral cap segment lingual thickness (1040) may be greater than the second dextral cap segment facial thickness (1050), as seen in FIG. 6.

In further embodiments still, seen well in FIGS. 1-3, the dextral segment (600) may further have a third dextral cap segment (900) having a third dextral internal cap segment surface (920), a third dextral external cap surface (960). There may be at least one dextral cap thickness (1000) formed collectively by elements (1070, 1080) seen in FIG. 6, and (1090), seen in FIG. 13; defined as the thickness of the orthotic (10) material, that is the distance between the third dextral internal cap segment surface (920) and the third dextral external cap segment surface (960), as seen in FIGS. 1 and 3.

In such embodiments, the third dextral internal cap surface (920), seen in FIG. 1, may have a third dextral internal cap segment lingual surface (922), a third dextral internal cap segment facial surface (924), and a third dextral internal cap segment occlusal surface (926), all seen in FIG. 2. The third dextral external cap segment surface (960), seen in FIG. 3, can include a third dextral external cap segment lingual surface (962), third dextral external cap segment facial surface (964), and a third dextral external cap segment occlusal surface (966), all seen in FIG. 5.

In these embodiments, the dextral cap segment thickness (1000) may include a third dextral cap segment lingual thickness (1070) and a third dextral cap segment facial thickness (1080), both seen in FIG. 6, and a third dextral cap segment occlusal thickness (1090), seen in FIG. 13; and the third dextral cap segment lingual thickness (1070) may be greater than the third dextral cap segment facial thickness (1080), all seen well in FIG. 6.

Figure 4:
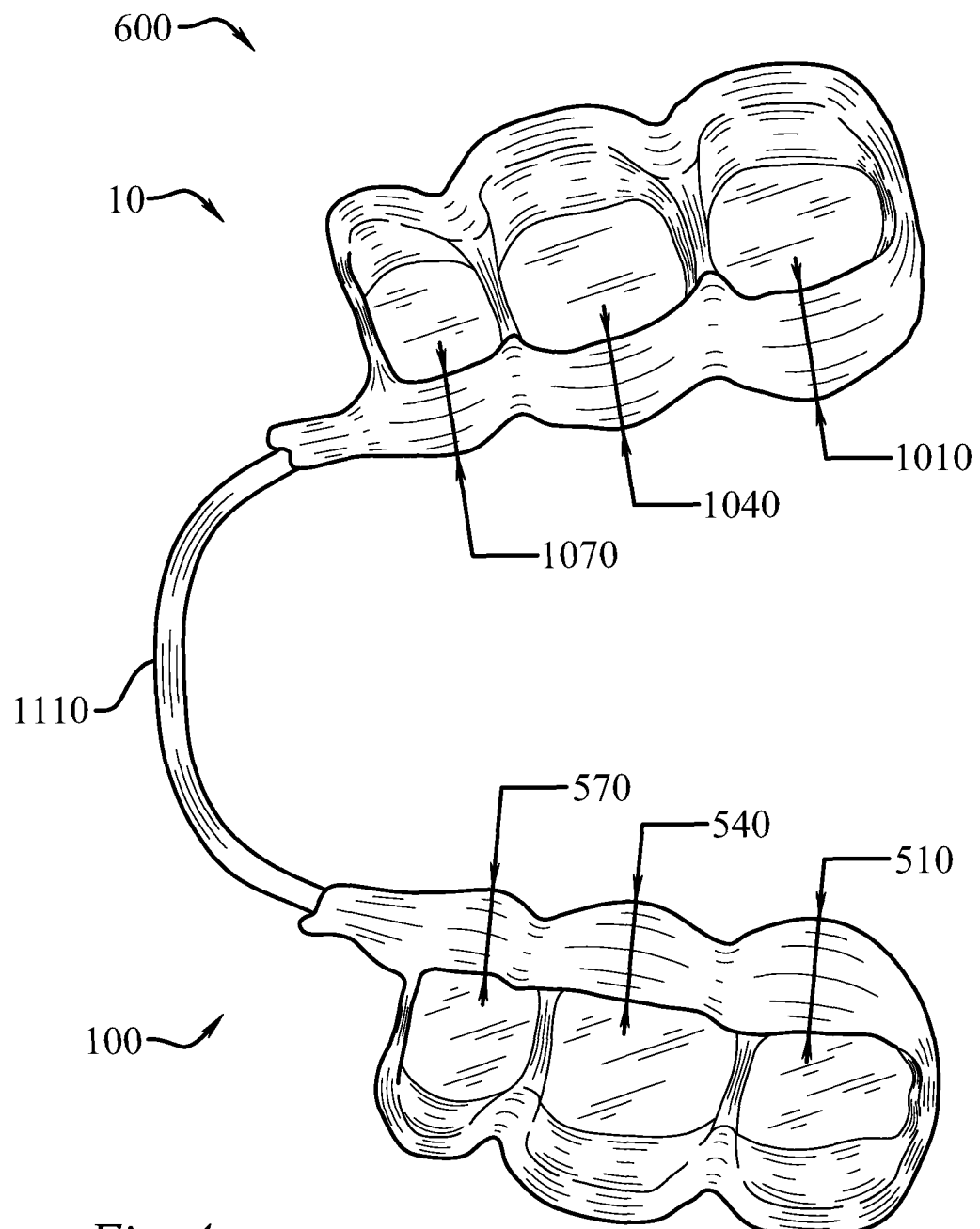
FIG. 4 is a another bottom view of the orthotic of FIG. 1.

One skilled in the art will recognize that in some preferred embodiments, there may be a progressive relationship between various thicknesses of the orthotic (10), seen well in FIGS. 4 and 6. In some embodiments, the second sinistral cap segment lingual thickness (540) may be less than the first sinistral cap segment lingual thickness (510), and in certain embodiments, the second sinistral cap segment lingual thickness (540) may be less than the first sinistral cap segment lingual thickness (510) by approximately 1 millimeter. In other embodiments, the third sinistral cap segment lingual thickness (570) may be less than the second sinistral cap segment lingual thickness (540), and in certain embodiments, the third sinistral cap segment lingual thickness (570) may be less than the second sinistral cap segment lingual thickness (540) by approximately 1 millimeter.

In other embodiments, also seen well in FIGS. 4 and 6, the second dextral cap segment lingual thickness (1040) may be less than the second dextral cap segment lingual thickness (1010), and in certain embodiments, the second dextral cap segment lingual thickness (1040) is less than the second dextral cap segment lingual thickness (1010) by approximately 1 millimeter. In certain embodiments, the third dextral cap segment lingual thickness (1070) may be less than the second dextral cap segment lingual thickness (1040), and in other embodiments, the third dextral cap segment lingual thickness (1070) may be less than the second dextral cap segment lingual thickness (1040) by approximately 1 millimeter There may be thickness relationships between potentially non-adjacent segments (200, 300, 400, 700, 800, 900), once again seen well in FIGS. 4 and 6. For example, in one embodiment, the third sinistral cap segment lingual thickness (570) may be less than the first sinistral cap segment lingual thickness (510) by approximately 2 millimeters. In other embodiments, the third dextral cap segment lingual thickness (1070) may be less than the first dextral cap segment lingual thickness (1010) by approximately 2 millimeters.

In a preferred embodiment, seen in FIG. 1, the orthotic (10) is a mandibular orthotic (10), where the sinistral segment (100) is a mandibular sinistral segment (100) and the dextral segment (600) is a mandibular dextral segment (600). The sinistral segment (100) and the dextral segment (600) may be joined, by way of example and not limitation only, by an incisor segment (1100) intended to at least partially cover one or more incisor teeth, as seen in FIG. 3, and in other embodiments, the sinistral segment (100) and the dextral segment (600) may be joined by such as an incisor bridge (1110) that bridges a distance between the segments (100, 600) but does not at least partially cover one or more incisor teeth, as seen in FIG. 4. In yet other embodiments, the segments (100, 600) may be totally separate, as seen in FIG. 7.

The orthotic (10) may be fully mandibular in nature, or in other embodiments, at least one mandibular segment (100, 600) may be coupled to at least one maxillary dental orthotic.

In one preferred, but not exclusive embodiment, seen in FIGS. 1-14, the dental orthotic (10) includes a sinistral segment (100) and a dextral segment (600), seen in FIGS. 1-3. The sinistral segment (100) further may have a first sinistral cap segment (200) having a first sinistral internal cap segment surface (220), a first sinistral external cap segment surface (260). There may be at least one sinistral cap segment thickness (500) defined as the thickness of the orthotic (10) between the first sinistral internal cap segment surface (220) and the first sinistral external cap segment surface (260), as seen in FIGS. 1 and 3.

The first sinistral internal cap segment surface (220), seen in FIG. 1, further may have, as seen in FIG. 2, a first sinistral internal cap segment lingual surface (222), a first sinistral internal cap segment facial surface (224), and a first sinistral internal cap segment occlusal surface (226). The first sinistral external cap segment surface (260), seen in FIG. 3, may have a first sinistral external cap segment lingual surface (262), first sinistral external cap segment facial surface (264), and a first sinistral external cap segment occlusal surface (266), seen in FIG. 5. The sinistral cap segment thickness (500) may further include a first sinistral cap segment lingual thickness (510) and a first sinistral cap segment facial thickness (520), seen in FIG. 6, and a first sinistral cap segment occlusal thickness (530), seen in FIG. 9.

In this embodiment, there may be a second sinistral cap segment (300) having a second sinistral internal cap segment surface (320), seen in FIG. 1, a second sinistral external cap segment surface (360), seen in FIG. 3, and at least one sinistral cap segment thickness (500) defined as the thickness of the orthotic (10) between the second sinistral internal cap segment surface (320) and the second sinistral external cap segment surface (360). The second sinistral internal cap segment surface (320) may further include a second sinistral internal cap segment lingual surface (322), a second sinistral internal cap segment facial surface (324), and a second sinistral internal cap segment occlusal surface (326), all as seen in FIG. 2.

The second sinistral external cap segment surface (360), seen in FIG. 3, further may have, as seen in FIG. 5, a second sinistral external cap segment lingual surface (362), second sinistral external cap segment facial surface (364), and a second sinistral external cap segment occlusal surface (366). The sinistral cap segment thickness (500) may further include a second sinistral cap segment lingual thickness (540) and a second sinistral cap segment facial thickness (550), seen in FIG. 6, and a second sinistral cap segment occlusal thickness (560), seen in FIG. 12.

The embodiment may further include a third sinistral cap segment (400), seen in FIG. 1, having a third sinistral internal cap segment surface (420), a third sinistral external cap segment surface (460), seen in FIG. 3, and at least one sinistral cap segment thickness (500) defined as the thickness of the orthotic (10) between the third sinistral internal cap segment surface (420) and the third sinistral external cap segment surface (460), as seen in FIGS. 1 and 3.

The third sinistral internal cap segment surface (420), seen in FIG. 1, further may have, as seen in FIG. 2, a third sinistral internal cap segment lingual surface (422), a third sinistral internal cap segment facial surface (424), and a third sinistral internal cap segment occlusal surface (426). The third sinistral external cap segment surface (460), seen in FIG. 3, may further include, as seen in FIG. 5, a third sinistral external cap segment lingual surface (462), third sinistral external cap segment facial surface (464), and a third sinistral external cap segment occlusal surface (466). The sinistral cap segment thickness (500) may further include a third sinistral cap segment lingual thickness (570) and a third sinistral external cap segment facial thickness (580), seen in FIG. 6, and a third sinistral cap segment occlusal thickness (590), seen in FIG. 14.

In an embodiment, seen in FIG. 1, the dextral segment (600) may further include a first dextral cap segment (700) having a first dextral internal cap segment surface (720), a first dextral external cap segment surface (760), seen in FIG. 3. There may be at least one dextral cap thickness (500), formed collectively by elements (1040, 1050), seen in FIG. 6, and (1060), seen in FIG. 11; defined as the thickness of the orthotic (10) between the first dextral internal cap segment surface (720) and the first dextral external cap segment surface (760), as seen in FIGS. 1 and 3.

The first dextral internal cap segment surface (720), seen in FIG. 1, further may have, seen in FIG. 2, a first dextral internal cap segment lingual surface (722), a first dextral internal cap segment facial surface (724), and a first dextral internal cap segment occlusal surface (726). The first dextral external cap segment surface (760), seen in FIG. 3, may further include a first dextral external cap segment lingual surface (762), first dextral external cap segment facial surface (764), and a first dextral external cap segment occlusal surface (766), seen in FIG. 5. The dextral cap segment thickness (500), formed collectively by elements (1010, 1020), seen in FIG. 6, and (1030), seen in FIG. 9, may further include a first dextral cap segment lingual thickness (1010) and a first dextral cap segment facial thickness (1020), seen in FIG. 6, and a first dextral cap segment occlusal thickness (1030), seen in FIG. 9.

There may be, in at least in a preferred embodiment, a second dextral cap segment (800), seen in FIG. 1, having a second dextral internal cap segment surface (820), a second dextral external cap segment surface (860), seen in FIG. 3. There may be at least one dextral cap segment thickness (500), formed collectively by elements (1040, 1050), seen in FIG. 6, and (1060), seen in FIG. 11; defined as the thickness of the orthotic (10) between the second dextral internal cap segment surface (820) and the second dextral external cap segment surface (860), as seen in FIGS. 1 and 3. The second dextral internal cap segment surface (820), seen in FIG. 1, further may have, as seen in FIG. 2, a second dextral internal cap segment lingual surface (822), a second dextral internal cap segment facial surface (824), and a second dextral internal cap segment occlusal surface (826). The second dextral external cap segment surface (860), seen in FIG. 3 may further include, as seen in FIG. 5, a second dextral external cap segment lingual surface (862), second dextral external cap segment facial surface (864), and a second dextral external cap segment occlusal surface (866). The dextral cap segment thickness (500), formed collectively by elements (1040, 1050), seen in FIG. 6 and (1060) seen in FIG. 11, may have a second dextral cap segment lingual thickness (1040) and a second dextral cap segment facial thickness (1050), as seen in FIG. 6, and a second dextral cap segment occlusal thickness (1060), as seen in FIG. 11.

Again at least in one embodiment, there may be a third dextral cap segment (900), seen in FIG. 1, having a third dextral internal cap segment surface (920), a third dextral external cap surface (960), seen in FIG. 3. There may be at least one dextral cap thickness (500), formed collectively by elements (1070, 1080), seen in FIG. 6, and (1090), seen in FIG. 13; defined as the thickness of the orthotic (10) between the third dextral internal cap segment surface (920) and the third dextral external cap segment surface (960), as seen in FIGS. 1 and 3. The third dextral internal cap surface (920), FIG. 1, may have, as seen in FIG. 2, a third dextral internal cap segment lingual surface (922), a third dextral internal cap segment facial surface (924), and a third dextral internal cap segment occlusal surface (926). The third dextral external cap segment surface (960), seen in FIG. 3, can have a third dextral external cap segment lingual surface (962), third dextral external cap segment facial surface (964), and a third dextral external cap segment occlusal surface (966), all as seen in FIG. 5. The dextral cap segment thickness (500), formed collectively by elements (1070, 1080), seen in FIG. 6, and (1090), seen in FIG. 13, may further include a third dextral cap segment lingual thickness (1070), a third dextral cap segment facial thickness (1080), and a third dextral cap segment occlusal thickness (1090).

In a preferred embodiment, seen in FIGS. 4 and 6, the second sinistral cap segment lingual thickness (540) may be less than the first sinistral cap segment lingual thickness (510) and the third sinistral cap segment lingual thickness (570) may be less than the second sinistral cap segment lingual thickness (540). Also, the second dextral cap segment lingual thickness (1040) may be less than the second dextral cap segment lingual thickness (1010) and the third dextral cap segment lingual thickness (1070) may be less than the second dextral cap segment lingual thickness (1040).

In some embodiments of the orthotic (10), also seen in FIGS. 4 and 6, the second sinistral cap segment lingual thickness (540) may be less than the first sinistral cap segment lingual thickness (510) by approximately 1 millimeter, while in some embodiments the third sinistral cap segment lingual thickness (570) may be less than the first sinistral cap segment lingual thickness (510) by approximately 2 millimeters.

In yet other embodiments, once again in FIGS. 4 and 6, the second dextral cap segment lingual thickness (1040) may be less than the second dextral cap segment lingual thickness (1010) by approximately 1 millimeter, while in some embodiments, the third dextral cap segment lingual thickness (1070) may be less than the first dextral cap segment lingual thickness (1010) by approximately 2 millimeters.

The orthotic (10) may be constructed, in an exemplary embodiment as follows. One skilled in the art, will of course, envision other methods and steps and they are all intended to be included in various embodiments.

A method for making a dental orthotic (10) may begin with in vivo reversibly molding at least one sinistral mandibular segment (100) to the teeth of a patient. The mandibular segment (100) may have at least one first sinistral cap segment lingual thickness (510) measured as the distance between a first sinistral internal cap lingual surface (222) and a first sinistral external cap lingual surface (262). Similarly, at least one dextral mandibular segment (600) may be in vivo molded to the teeth of a patient. This dextral mandibular segment (600) may have at least one first dextral cap segment lingual thickness (1010), measured as the distance between a first dextral internal cap segment lingual surface (722) and a first dextral external cap segment lingual surface (762).

The at least one molded sinistral mandibular segment (100) and the at least one dextral mandibular segment (600) may be placed on the teeth of the patient accompanied by real-time observation a blood oxygen saturation in the patient, by means as would be known to one skilled in the art, such as transcutaneous blood oxygen monitoring.

The at least one sinistral mandibular segment (100) and the at least one dextral mandibular segment (600) may then be removed from the teeth of the patient, and additional material, which may be the same material of which the orthotic (10) was molded, may be added to the first sinistral external cap segment lingual surface (262) to increase the at least one first sinistral cap segment lingual thickness (510) by at least 10% and adding material to the first dextral internal cap segment lingual surface (762) to increase the first dextral cap segment lingual thickness (1010) by at least 10%.

The at least one sinistral mandibular segment (100) and the at least one dextral mandibular segment (600) may be returned to the teeth of the patient; a repeated, real-time observations of the blood oxygen saturation in the patient are made. The steps of removing the orthotic (10) and adding material to increase the at least one first sinistral cap segment lingual thickness (510) by at least 10% and adding material to increase the first dextral cap segment lingual thickness (1010) by at least 10% may be repeated until repeated steps do not result in an increase in the patient's blood oxygen saturation of at least 1%.

Numerous alterations, modifications, and variations of the preferred embodiments disclosed herein will be apparent to those skilled in the art and they are all anticipated and contemplated to be within the spirit and scope of the disclosed dental orthotic (10). For example, although specific embodiments have been described in detail, those with skill in the art will understand that the preceding embodiments and variations can be modified to incorporate various types of substitute and or additional or alternative materials, relative arrangement of elements, and dimensional configurations. Accordingly, even though only few variations of the dental orthotic (10) are described herein, it is to be understood that the practice of such additional modifications and variations and the equivalents thereof, are within the spirit and scope of the dental orthotic (10) as disclosed herein. The corresponding structures, materials, acts, and equivalents of all means or step plus function elements in the claims below are intended to include any structure, material, or acts for performing the functions in combination with other claimed elements as specifically claimed.

I claim:

1. A dental orthotic (10) comprising; a sinistral segment (100) and a dextral segment (600); wherein,
   a) the sinistral segment (100) further comprises a first sinistral cap segment (200) having a first sinistral internal cap segment surface (220), a first sinistral external cap segment surface (260) and at least one sinistral cap segment thickness (500) therebetween; and
      i) the first sinistral internal cap segment surface (220) further comprises a first sinistral internal cap segment lingual surface (222), a first sinistral internal cap segment facial surface (224), and a first sinistral internal cap segment occlusal surface (226), and
  ii) the first sinistral external cap segment surface (260) further comprises a first sinistral external cap segment lingual surface (262), first sinistral external cap segment facial surface (264), and a first sinistral external cap segment occlusal surface (266); and
  iii) the sinistral cap segment thickness (500) further comprises a first sinistral cap segment lingual thickness (510), a first sinistral cap segment facial thickness (520), and a first sinistral cap segment occlusal thickness (530); and
 b) the sinistral segment (100) further comprises a second sinistral cap segment (300) having a second sinistral internal cap segment surface (320), a second sinistral external cap segment surface (360) and at least one sinistral cap segment thickness (500) therebetween; and
  i) the second sinistral internal cap segment surface (320) further comprises a second sinistral internal cap segment lingual surface (322), a second sinistral internal cap segment facial surface (324), and a second sinistral internal cap segment occlusal surface (326), and
  ii) the second sinistral external cap segment surface (360) further comprises a second sinistral external cap segment lingual surface (362), second sinistral external cap segment facial surface (364), and a second sinistral external cap segment occlusal surface (366); and
  iii) the sinistral cap segment thickness (500) further comprises a second sinistral cap segment lingual thickness (540), a second sinistral cap segment facial thickness (550), and a second sinistral cap segment occlusal thickness (560); and d) the second sinistral cap segment lingual thickness (540) is greater than the second sinistral cap segment facial thickness (550), and
 c) the dextral segment (600) further comprises a first dextral cap segment (700) having a first dextral internal cap segment surface (720), a first dextral external cap segment surface (760) and at least one dextral cap thickness (1000) therebetween; and
  i) the first dextral internal cap segment surface (720) further comprises a first dextral internal cap segment lingual surface (722), a first dextral internal cap segment facial surface (724), and a first dextral internal cap segment occlusal surface (726), and
  ii) the first dextral external cap segment surface (760) further comprises a first dextral external cap segment lingual surface (762), first dextral external cap segment facial surface (764), and a first dextral external cap segment occlusal surface (766);
  iii) the dextral cap segment thickness (1000) further comprises a first dextral cap segment lingual thickness (1010), a first dextral cap segment facial thickness (1020), and a first dextral cap segment occlusal thickness (1030), and
 d) the first sinistral cap segment lingual thickness (510) is greater than the first sinistral cap segment facial thickness (520); and
 e) the first dextral cap segment lingual thickness (1010) is greater than the first dextral cap segment facial thickness (1020).

2. The device according to claim 1, wherein the dextral segment (600) further comprises a second dextral cap segment (800) having a second dextral internal cap segment surface (820), a second dextral external cap segment surface (860) and at least one dextral cap segment thickness (1000) therebetween; and
 a) the second dextral internal cap segment surface (820) further comprises a second dextral internal cap segment lingual surface (822), a second dextral internal cap segment facial surface (824), and a second dextral internal cap segment occlusal surface (826), and
 b) the second dextral external cap segment surface (860) further comprises a second dextral external can segment lingual surface (862) second dextral external can segment facial surface (864), and a second dextral external cap segment occlusal surface (866); and
 c) the dextral cap segment thickness (1000) further comprises a second dextral cap segment lingual thickness (1040), a second dextral cap segment facial thickness (1050), and a second dextral cap segment occlusal thickness (1060); and
 d) the second dextral cap segment lingual thickness (1040) is greater than the second dextral cap segment facial thickness (1050).

3. The device according to claim 2, wherein the dextral segment (600) further comprises a third dextral cap segment (900) having a third dextral internal cap segment surface (920), a third dextral external cap surface (960) and at least one dextral cap thickness (1000) therebetween; and
 a) the third dextral internal cap surface (920) further comprises a third dextral internal cap segment lingual surface (922), a third dextral internal cap segment facial surface (924), and a third dextral internal cap segment occlusal surface (926), and
 b) the third dextral external cap segment surface (960) further comprises a third dextral external cap segment lingual surface (962), third dextral external cap segment facial surface (964), and a third dextral external cap segment occlusal surface (966); and
 c) the dextral cap segment thickness (1000) further comprises a third dextral cap segment lingual thickness (1070), a third dextral cap segment facial thickness (1080), and a third dextral cap segment occlusal thickness (1090); and
 d) the third dextral cap segment lingual thickness (1070) is greater than the third dextral cap segment facial thickness (1080).

4. The device according to claim 3, wherein the third dextral cap segment lingual thickness (1070) is less than the second dextral cap segment lingual thickness (1040).

5. The device according to claim 4, wherein the third dextral cap segment lingual thickness (1070) is less than the second dextral cap segment lingual thickness (1040) by approximately 1 millimeter.

6. The device according to claim 4, wherein the third dextral cap segment lingual thickness (1070) is less than the first dextral cap segment lingual thickness (1010) by approximately 2 millimeters.

7. The device according to claim 2, wherein the second dextral cap segment lingual thickness (1040) is less than the second dextral cap segment lingual thickness (1010).

8. The device according to claim 7, wherein the second dextral cap segment lingual thickness (1040) is less than the second dextral cap segment lingual thickness (1010) by approximately 1 millimeter.

9. The device according to claim 1, wherein the sinistral segment (100) further comprises a third sinistral cap segment (400) having a third sinistral internal cap segment surface (420), a third sinistral external cap segment surface (460) and at least one sinistral cap segment thickness (500) therebetween; and
    a) the third sinistral internal cap segment surface (420) further comprises a third sinistral internal cap segment lingual surface (422), a third sinistral internal cap segment facial surface (424), and a third sinistral internal cap segment occlusal surface (426), and
    b) the third sinistral external cap segment surface (460) further comprises a third sinistral external cap segment lingual surface (462), third sinistral external cap segment facial surface (464), and a third sinistral external cap segment occlusal surface (466); and
    c) the sinistral cap segment thickness (500) further comprises a third sinistral cap segment lingual thickness (570), a third sinistral external cap segment facial thickness (580), and a third sinistral cap segment occlusal thickness (590); and
    d) the third sinistral cap segment lingual thickness (570) is greater than the third sinistral external cap segment facial thickness (580).

10. The device according to claim 9, wherein the third sinistral cap segment lingual thickness (570) is less than the second sinistral cap segment lingual thickness (540).

11. The device according to claim 10, wherein the third sinistral cap segment lingual thickness (570) is less than the second sinistral cap segment lingual thickness (540) by approximately 1 millimeter.

12. The device according to claim 10, wherein the third sinistral cap segment lingual thickness (570) is less than the first sinistral cap segment lingual thickness (510) by approximately 2 millimeters.

13. The device according to claim 1, wherein the second sinistral cap segment lingual thickness (540) is less than the first sinistral cap segment lingual thickness (510).

14. The device according to claim 13, wherein the second sinistral cap segment lingual thickness (540) is less than the first sinistral cap segment lingual thickness (510) by approximately 1 millimeter.

15. The device according to claim 1, wherein the sinistral segment (100) is a mandibular sinistral segment (100) and the dextral segment (600) is a mandibular dextral segment (600).

16. The device according to claim 15, wherein at least one mandibular segment selected from the group of mandibular segments (100, 600) consisting of the mandibular sinistral segment (100) and the mandibular dextral segment (600) is coupled to at least one maxillary dental orthotic.

17. The device according to claim 1, wherein the sinistral segment (100) and the dextral segment (600) are joined by an incisor segment (1000).

18. The device according to claim 17, wherein the incisor segment further comprises an incisor bridge (1010).

19. A dental orthotic (10) comprising; a sinistral segment (100) and a dextral segment (600); wherein,
    a) the sinistral segment (100) further comprises a first sinistral cap segment (200) having a first sinistral internal cap segment surface (220), a first sinistral external cap segment surface (260) and at least one sinistral cap segment thickness (500) therebetween; and
        i) the first sinistral internal cap segment surface (220) further comprises a first sinistral internal cap segment lingual surface (222), a first sinistral internal cap segment facial surface (224), and a first sinistral internal cap segment occlusal surface (226), and
        ii) the first sinistral external cap segment surface (260) further comprises a first sinistral external cap segment lingual surface (262), first sinistral external cap segment facial surface (264), and a first sinistral external cap segment occlusal surface (266); and
        iii) the sinistral cap segment thickness (500) further comprises a first sinistral cap segment lingual thickness (510), a first sinistral cap segment facial thickness (520), and a first sinistral cap segment occlusal thickness (530);
    b) the dextral segment (600) further comprises a first dextral cap segment (700) having a first dextral internal cap segment surface (720), a first dextral external cap segment surface (760) and at least one dextral cap thickness (1000) therebetween; and
        i) the first dextral internal cap segment surface (720) further comprises a first dextral internal cap segment lingual surface (722), a first dextral internal cap segment facial surface (724), and a first dextral internal cap segment occlusal surface (726), and
        ii) the first dextral external cap segment surface (760) further comprises a first dextral external cap segment lingual surface (762), first dextral external cap segment facial surface (764), and a first dextral external cap segment occlusal surface (766);
        iii) the dextral cap segment thickness (1000) further comprises a first dextral cap segment lingual thickness (1010), a first dextral cap segment facial thickness (1020), and a first dextral cap segment occlusal thickness (1030), and
    c) the dextral segment (600) further comprises a second dextral cap segment (800) having a second dextral internal cap segment surface (820), a second dextral external cap segment surface (860) and at least one dextral cap segment thickness (1000) therebetween; and
        i) the second dextral internal cap segment surface (820) further comprises a second dextral internal cap segment lingual surface (822), a second dextral internal cap segment facial surface (824), and a second dextral internal cap segment occlusal surface (826), and
        ii) the second dextral external cap segment surface (860) further comprises a second dextral external cap segment lingual surface (862), second dextral external cap segment facial surface (864), and a second dextral external cap segment occlusal surface (866); and
        iii) the dextral cap segment thickness (1000) further comprises a second dextral cap segment lingual thickness (1040), a second dextral cap segment facial thickness (1050), and a second dextral cap segment occlusal thickness (1060); and
        iv) the second dextral cap segment lingual thickness (1040) is greater than the second dextral cap segment facial thickness (1050), and
    d) the first sinistral cap segment lingual thickness (510) is greater than the first sinistral cap segment facial thickness (520); and
    e) the first dextral cap segment lingual thickness (1010) is greater than the first dextral cap segment facial thickness (1020).

20. The device according to claim 19, wherein the dextral segment (600) further comprises a third dextral cap segment (900) having a third dextral internal cap segment surface (920), a third dextral external cap surface (960) and at least one dextral cap thickness (1000) therebetween; and
    a) the third dextral internal cap surface (920) further comprises a third dextral internal cap segment lingual surface (922), a third dextral internal cap segment facial surface (924), and a third dextral internal cap segment occlusal surface (926), and b) the third dextral external cap segment surface (960) further comprises a third dextral external cap segment lingual surface (962), third dextral external cap segment facial surface (964), and a third dextral external cap segment occlusal surface (966); and c) the dextral cap segment thickness (1000) further comprises a third dextral cap segment lingual thickness (1070), a third dextral cap segment facial thickness (1080), and a third dextral cap segment occlusal thickness (1090); and d) the third dextral cap segment lingual thickness (1070) is greater than the third dextral cap segment facial thickness (1080).

21. The device according to claim 20, wherein the third dextral cap segment lingual thickness (1070) is less than the second dextral cap segment lingual thickness (1040).

22. The device according to claim 20, wherein the third dextral cap segment lingual thickness (1070) is less than the second dextral cap segment lingual thickness (1040) by approximately 1 millimeter.

23. The device according to claim 20, wherein the third dextral cap segment lingual thickness (1070) is less than the first dextral cap segment lingual thickness (1010) by approximately 2 millimeters.

24. The device according to claim 19, wherein the second dextral cap segment lingual thickness (1040) is less than the second dextral cap segment lingual thickness (1010).

25. The device according to claim 19, wherein the second dextral cap segment lingual thickness (1040) is less than the second dextral cap segment lingual thickness (1010) by approximately 1 millimeter.

26. A dental orthotic (10) comprising; a sinistral segment (100) and a dextral segment (600); wherein the sinistral segment (100) further comprises:

a) a first sinistral cap segment (200) having a first sinistral internal cap segment surface (220), a first sinistral external cap segment surface (260) and at least one sinistral cap segment thickness (500) therebetween; and i) the first sinistral internal cap segment surface (220) further comprises a first sinistral internal cap segment lingual surface (222), a first sinistral internal cap segment facial surface (224), and a first sinistral internal cap segment occlusal surface (226), and ii) the first sinistral external cap segment surface (260) further comprises a first sinistral external cap segment lingual surface (262), first sinistral external cap segment facial surface (264), and a first sinistral external cap segment occlusal surface (266); and iii) the sinistral cap segment thickness (500) further comprises a first sinistral cap segment lingual thickness (510), a first sinistral cap segment facial thickness (520), and a first sinistral cap segment occlusal thickness (530); and b) a second sinistral cap segment (300) having a second sinistral internal cap segment surface (320), a second sinistral external cap segment surface (360) and at least one sinistral cap segment thickness (500) therebetween; and i) the second sinistral internal cap segment surface (320) further comprises a second sinistral internal cap segment lingual surface (322), a second sinistral internal cap segment facial surface (324), and a second sinistral internal cap segment occlusal surface (326), and ii) the second sinistral external cap segment surface (360) further comprises a second sinistral external cap segment lingual surface (362), second sinistral external cap segment facial surface (364), and a second sinistral external cap segment occlusal surface (366); and iii) the sinistral cap segment thickness (500) further comprises a second sinistral cap segment lingual thickness (540), a second sinistral cap segment facial thickness (550), and a second sinistral cap segment occlusal thickness (560); and c) a third sinistral cap segment (400) having a third sinistral internal cap segment surface (420), a third sinistral external cap segment surface (460) and at least one sinistral cap segment thickness (500) therebetween; and i) the third sinistral internal cap segment surface (420) further comprises a third sinistral internal cap segment lingual surface (422), a third sinistral internal cap segment facial surface (424), and a third sinistral internal cap segment occlusal surface (426), and ii) the third sinistral external cap segment surface (460) further comprises a third sinistral external cap segment lingual surface (462), third sinistral external cap segment facial surface (464), and a third sinistral external cap segment occlusal surface (466); and iii) the sinistral cap segment thickness (500) further comprises a third sinistral cap segment lingual thickness (570), a third sinistral external cap segment facial thickness (580), and a third sinistral cap segment occlusal thickness (590); and the dextral segment (600) further comprises;

a) the dextral segment (600) further comprises a first dextral cap segment (700) having a first dextral internal cap segment surface (720), a first dextral external cap segment surface (760) and at least one dextral cap thickness (1000) therebetween; and i) the first dextral internal cap segment surface (720) further comprises a first dextral internal cap segment lingual surface (722), a first dextral internal cap segment facial surface (724), and a first dextral internal cap segment occlusal surface (726), and ii) the first dextral external cap segment surface (760) further comprises a first dextral external cap segment lingual surface (762), first dextral external cap segment facial surface (764), and a first dextral external cap segment occlusal surface (766);

iii) the dextral cap segment thickness (1000) further comprises a first dextral cap segment lingual thickness (1010), a first dextral cap segment facial thickness (1020), and a first dextral cap segment occlusal thickness (1030), and b) a second dextral cap segment (800) having a second dextral internal cap segment surface (820), a second dextral external cap segment surface (860) and at least one dextral cap segment thickness (1000) therebetween; and i) the second dextral internal cap segment surface (820) further comprises a second dextral internal cap segment lingual surface (822), a second dextral internal cap segment facial surface (824), and a second dextral internal cap segment occlusal surface (826), and ii) the second dextral external cap segment surface (860) further comprises a second dextral external cap segment lingual surface (862), second dextral external cap segment facial surface (864), and a second dextral external cap segment occlusal surface (866);

iii) the dextral cap segment thickness (1000) further comprises a second dextral cap segment lingual thickness (1040), a second dextral cap segment facial thickness (1050), and a second dextral cap segment occlusal thickness (1060); and c) a third dextral cap segment (900) having a third dextral internal cap segment surface (920), a third dextral external cap surface (960) and at least one dextral cap thickness (1000) therebetween; and i) the third dextral internal cap surface (920) further comprises a third dextral internal cap segment lingual surface (922), a third dextral internal cap segment facial surface (924), and a third dextral internal cap segment occlusal surface (926), and ii) the third dextral external cap segment surface (960) further comprises a third dextral external cap segment lingual surface (962), third dextral external cap segment facial surface (964), and a third dextral external cap segment occlusal surface (966); and iii) the dextral cap segment thickness (1000) further comprises a third dextral cap segment lingual thickness (1070), a third dextral cap segment facial thickness (1080), and a third dextral cap segment occlusal thickness (1090); and the second sinistral cap segment lingual thickness (540) is less than the first sinistral cap segment lingual thickness (510);

the third sinistral cap segment lingual thickness (570) is less than the second sinistral cap segment lingual thickness (540), the second dextral cap segment lingual thickness (1040) is less than the second dextral cap segment lingual thickness (1010), and the third dextral cap segment lingual thickness (1070) is less than the second dextral cap segment lingual thickness (1040).

27. The device according to claim 26, wherein the second sinistral cap segment lingual thickness (540) is less than the first sinistral cap segment lingual thickness (510) by approximately 1 millimeter.

28. The device according to claim 26, wherein the third sinistral cap segment lingual thickness (570) is less than the first sinistral cap segment lingual thickness (510) by approximately 2 millimeters.

29. The device according to claim 26, wherein the second dextral cap segment lingual thickness (1040) is less than the second dextral cap segment lingual thickness (1010) by approximately 1 millimeter.

30. The device according to claim 26, wherein the third dextral cap segment lingual thickness (1070) is less than the first dextral cap segment lingual thickness (1010) by approximately 2 millimeters.

31. The device according to claim 26, wherein the third dextral cap segment lingual thickness (1070) is less than the first dextral cap segment lingual thickness (1010) by approximately 2 millimeters.

\* \* \* \* \*